US011857717B2

(12) United States Patent
Taurino

(10) Patent No.: US 11,857,717 B2
(45) Date of Patent: Jan. 2, 2024

(54) AEROSOL GENERATING SYSTEM WITH ENHANCED AEROSOL DELIVERY

(71) Applicant: PHILIP MORRIS PRODUCTS S.A., Neuchatel (CH)

(72) Inventor: Irene Taurino, Lausanne (CH)

(73) Assignee: Philip Morris Products S.A., Neuchatel (CH)

( * ) Notice: Subject to any disclaimer, the term of this patent is extended or adjusted under 35 U.S.C. 154(b) by 552 days.

(21) Appl. No.: 16/973,588

(22) PCT Filed: Jun. 26, 2019

(86) PCT No.: PCT/EP2019/066996
§ 371 (c)(1),
(2) Date: Dec. 9, 2020

(87) PCT Pub. No.: WO2020/002425
PCT Pub. Date: Jan. 2, 2020

(65) Prior Publication Data
US 2021/0212368 A1  Jul. 15, 2021

(30) Foreign Application Priority Data
Jun. 29, 2018  (EP) .................................... 18180834

(51) Int. Cl.
*A24F 40/48* (2020.01)
*A61M 11/04* (2006.01)
(Continued)

(52) U.S. Cl.
CPC ........... *A61M 11/042* (2014.02); *A24F 40/30* (2020.01); *A24F 40/42* (2020.01); *A24F 40/465* (2020.01);
(Continued)

(58) Field of Classification Search
None
See application file for complete search history.

(56) References Cited

U.S. PATENT DOCUMENTS 9,532,603 B2 * 1/2017 Plojoux ................. A24F 40/485
10,028,535 B2  7/2018 Mironov
(Continued)

FOREIGN PATENT DOCUMENTS

CN  104994757 A * 10/2015 ............. A24F 40/30
CN  107921224 A *  4/2018 ........... A24B 15/167
(Continued)

OTHER PUBLICATIONS

Search Report and Written Opinion for PCT/EP2019/066996 dated Sep. 24, 2019 (10 pages).
(Continued)

*Primary Examiner* — Tho D Ta
(74) *Attorney, Agent, or Firm* — Mueting Raasch Group

(57) ABSTRACT

A cartridge for use in an aerosol-generating system, the cartridge comprising: a first compartment having a first air inlet and a first air outlet, the first compartment containing a nicotine source; and a second compartment having a second air inlet and a second air outlet, the second compartment containing an acid source; wherein the first compartment comprises a first air flow channel extending from the first air inlet, or the first air outlet, longitudinally along at least a portion of the first compartment, wherein the first air flow channel is adjacent to and in fluid communication with the nicotine source; or wherein the second compartment comprises a second air flow channel extending from the second air inlet, or the second air outlet, longitudinally along at least a portion of the second compartment, wherein the second air flow channel is adjacent to and in fluid communication with the acid source; or wherein the first compartment comprises a first air flow channel extending
(Continued)

from the first air inlet, or the first air outlet, longitudinally along at least a portion of the first compartment, wherein the first air flow channel is adjacent to and in fluid communication with the nicotine source; and the second compartment comprises a second airflow channel extending from the second air inlet, or the second air outlet, longitudinally along at least a portion of the second compartment, wherein the second air flow channel is adjacent to and in fluid communication with the acid source.

12 Claims, 10 Drawing Sheets

(51) Int. Cl.
  *A24F 40/30* (2020.01)
  *A24F 40/42* (2020.01)
  *A24F 40/465* (2020.01)
  *H05B 6/10* (2006.01)
  *A24F 40/10* (2020.01)
(52) U.S. Cl.
  CPC ............. *A24F 40/48* (2020.01); *H05B 6/105* (2013.01); *A24F 40/10* (2020.01)

(56) References Cited

U.S. PATENT DOCUMENTS

| | | | |
|---|---|---|---|
| 10,076,140 | B2 | 9/2018 | Silvestrini |
| 2016/0331032 | A1 * | 11/2016 | Malgat .................... A24B 3/14 |

FOREIGN PATENT DOCUMENTS

| | | | | |
|---|---|---|---|---|
| JP | 2017-519492 | | 7/2017 | |
| JP | 2017-524353 | | 8/2017 | |
| KR | 20160145838 A | * | 12/2016 | |
| WO | WO 2008/121610 | | 10/2008 | |
| WO | WO 2015/000974 | | 1/2015 | |
| WO | WO-2015082649 A1 | * | 6/2015 | ........... A24B 15/167 |
| WO | WO-2016124550 A1 | * | 8/2016 | ............. A24F 40/10 |
| WO | WO 2017/029268 | | 2/2017 | |
| WO | WO 2017/036950 | | 3/2017 | |
| WO | WO 2017/108987 | | 6/2017 | |
| WO | WO 2017/211600 | | 12/2017 | |
| WO | WO 2018/099999 | | 6/2018 | |

OTHER PUBLICATIONS

Office Action issued in Japan for Application No. 2020-568769 dated May 9, 2023 (4 pages). English translation included.

* cited by examiner

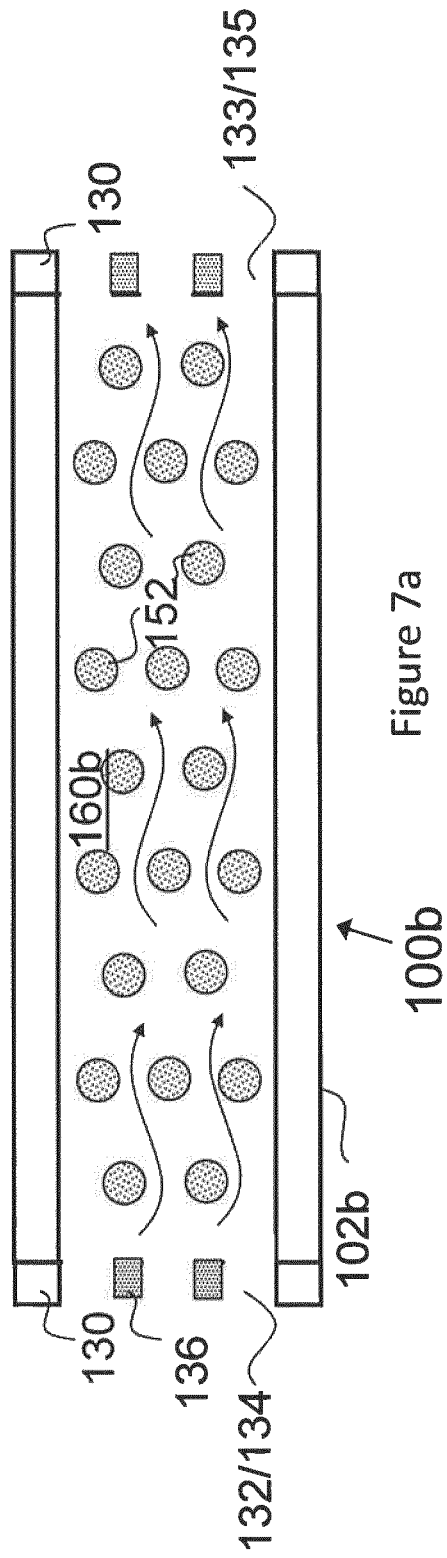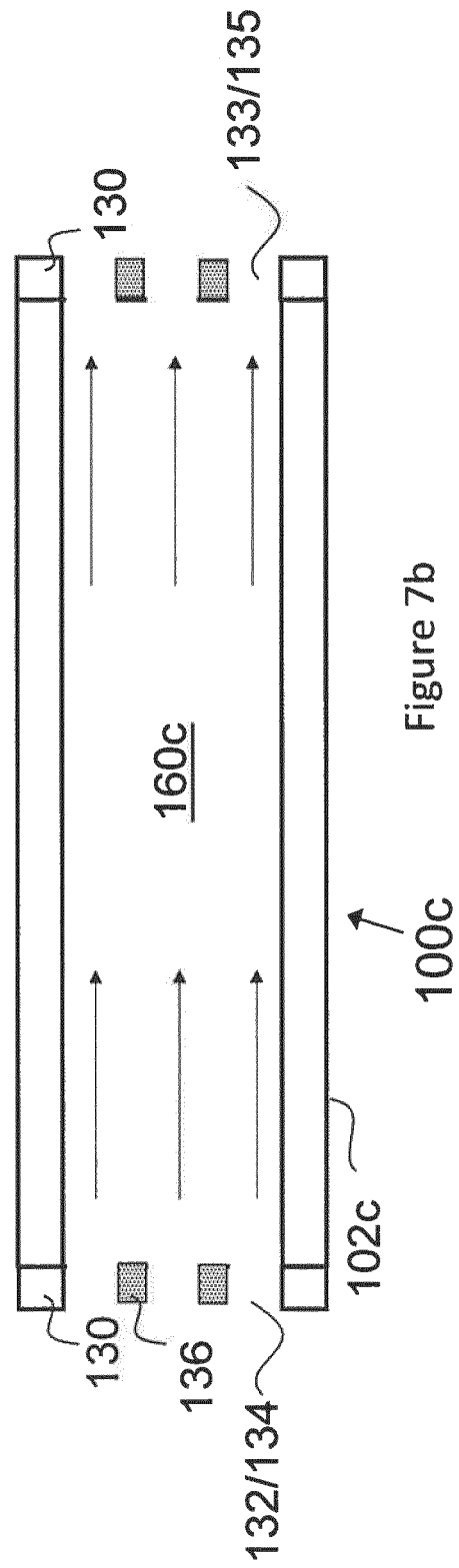

AEROSOL GENERATING SYSTEM WITH ENHANCED AEROSOL DELIVERY

This application is a U.S. National Stage Application of International Application No. PCT/EP2019/066996 filed Jun. 26, 2019, which was published in English on Jan. 2, 2020 as International Publication No. WO 2020/002425 A1. International Application No. PCT/EP2019/066996 claims priority to European Application No. 18180834.6 filed Jun. 29, 2018.

The present specification relates to a cartridge for use in an aerosol-generating device and an aerosol-generating system comprising such a cartridge. In particular, the invention relates to a cartridge assembly that provides enhanced aerosol delivery from a nicotine source and an acid source.

In some handheld aerosol-generating devices, an electrical heater is used for heating a nicotine source and a volatile delivery enhancing compound, for example an acid source. In these aerosol-generating devices, vaporised nicotine and acid reacts with each other in the gas phase to form an aerosol of nicotine salt particles that is inhaled by a user.

Differences between the vapour concentrations of nicotine and the acid in such devices may disadvantageously lead to an unfavourable reaction stoichiometry or the delivery of excess reactant, such as unreacted nicotine vapour or unreacted acid vapour to a user. Consequently, to balance the concentration of acid vapour and nicotine vapour to yield an efficient reaction stoichiometry, it may be necessary to heat the nicotine source and the acid source of devices disclosed in WO 2008/121610 A1 to different temperatures.

WO2017/108987 A1 discloses a cartridge assembly comprising a plurality of air inlets with different cross-sectional flow area. This allows the ratio of air supply flowing through different carrier materials impregnated with respective nicotine source and acid source to be controlled. With this arrangement, both the nicotine source and the acid source may be heated by the same heating element to the same temperature.

However, the systems described in the prior art still deliver limited amounts of aerosol to the user. Therefore, it would be desirable to provide an aerosol-generating device that provides an improved rate of aerosol delivery to the users in comparison to the prior art nicotine-acid reaction devices.

According to an aspect of the present invention there is provided a cartridge for use in an aerosol-generating system, the cartridge comprising: a first compartment having a first air inlet and a first air outlet, the first compartment containing a nicotine source; and a second compartment having a second air inlet and a second air outlet, the second compartment containing an acid source; wherein the first compartment comprises a first air flow channel extending from the first air inlet, or the first air outlet, longitudinally along at least a portion of the first compartment, wherein the first air flow channel is adjacent to and in fluid communication with the nicotine source; or wherein the second compartment comprises a second air flow channel extending from the second air inlet, or the second air outlet, longitudinally along at least a portion of the second compartment, wherein the second air flow channel is adjacent to and in fluid communication with the acid source; or wherein the first compartment comprises a first air flow channel extending from the first air inlet, or the first air outlet, longitudinally along at least a portion of the first compartment, wherein the first airflow channel is adjacent to and in fluid communication with the nicotine source; and the second compartment comprises a second air flow channel extending from the second air inlet, or the second air outlet, longitudinally along at least a portion of the second compartment, wherein the second air flow channel is adjacent to and in fluid communication with the acid source.

In use, a first air stream and a second air stream may be drawn through the first compartment and the second compartment respectively. Nicotine vapour is released from the nicotine source in the first compartment into the first air stream and acid vapour is released from the lactic acid source in the second compartment into the second air stream. The nicotine vapour in the first air stream may react with the acid vapour in the second air stream in the gas phase to form an aerosol of nicotine salt particles. The nicotine salt particles may be nicotine lactate salt. The aerosol-generating system may provide separate compartments for vaporisation of nicotine and acid. The aerosol-generating system may comprise a further compartment for reaction of the nicotine and acid vapours to form the aerosol. The aerosol-generating system may comprise a proximal end having a mouthpiece. In use, the aerosol containing nicotine salt particles may be drawn through the aerosol-generating system through the mouthpiece. The aerosol-generating system may comprise a distal end opposed to the proximal end.

As used herein with reference to the invention, the terms "proximal", "distal", "upstream" and "downstream" are used to describe the relative positions of components, or portions of components, of the cartridge and aerosol-generating system.

The aerosol-generating system according to the invention comprises a proximal end through which, in use, an aerosol of nicotine salt particles exits the aerosol-generating system for delivery to a user. The proximal end may also be referred to as the mouth end. In use, a user draws on the proximal end of the aerosol-generating system in order to inhale an aerosol generated by the aerosol-generating system. The aerosol-generating system comprises a distal end opposed to the proximal end.

When a user draws on the proximal end of the aerosol-generating system, air is drawn into the aerosol-generating system, passes through the cartridge and exits the aerosol-generating system at the proximal end thereof. Components, or portions of components, of the aerosol-generating system may be described as being upstream or downstream of one another based on their relative positions between the proximal end and the distal end of the aerosol-generating system along an airflow path.

The first air outlet of the first compartment of the cartridge is located at the proximal end of the first compartment of the cartridge. The first air inlet of the first compartment of the cartridge is located upstream of the first air outlet of the first compartment of the cartridge. The second air outlet of the second compartment of the cartridge is located at the proximal end of the second compartment of the cartridge. The second air inlet of the second compartment of the cartridge is located upstream of the second air outlet of the second compartment of the cartridge.

As used herein with reference to the invention, the term "longitudinal" is used to describe the direction between the proximal end and the opposed distal end of the cartridge or aerosol-generating system and the term "transverse" is used to describe the direction perpendicular to the longitudinal direction.

As used herein with reference to the invention, the term "length" is used to describe the maximum longitudinal dimension of components, or portions of components, of the cartridge or aerosol-generating system parallel to the longitudinal axis between the proximal end and the opposed distal end of the cartridge or aerosol-generating system.

As used herein with reference to the invention, the terms "height" and "width" are used to describe the maximum transverse dimensions of components, or portions of components, of the cartridge or aerosol-generating system perpendicular to the longitudinal axis of the cartridge or aerosol-generating system. Where the height and width of components, or portions of components, of the cartridge or aerosol-generating system are not the same, the term "width" is used to refer to the larger of the two transverse dimensions perpendicular to the longitudinal axis of the cartridge or aerosol-generating system.

The aerosol-generating system may be an electrically operated aerosol-generating system, and may include additional components, such as a charging unit for recharging an on-board electric power supply in an electrically operated aerosol-generating device to which the cartridge connects.

As used herein, a 'cartridge' relates to a disposable, or at least a replaceable part, in the aerosol-generating system. The cartridge may be replaced after a single session of use, or it may be replaced after a plurality of sessions of use. The cartridge may comprise at least the nicotine source and the acid source each contained in a separate compartment. Advantageously, by providing the nicotine source and the lactic acid source in separate compartments with separate air inlets and separate air outlets, the reaction stoichiometry between the nicotine and the lactic acid may be better controlled or balanced. This is because the volumetric flow rate in first compartment and the second compartment of the cartridge may be separately controlled. The cartridge according to the present invention may comprise more than one air flow channel in the first compartment containing the nicotine source. The cartridge may comprise more than one air flow channel in the second compartment containing the acid source. The cartridge may comprise further compartments for containing further sources in addition to the nicotine and acid sources. The further compartments may also comprise one or more air flow channels. The cartridge may comprise further components, such as a heating element or a sensor.

The first air outlet of the first compartment of the cartridge may be located at the proximal end of the first compartment of the cartridge. The first air inlet of the first compartment of the cartridge may be located upstream of the first air outlet of the first compartment of the cartridge. The second air outlet of the second compartment of the cartridge may be located at the proximal end of the second compartment of the cartridge. The second air inlet of the second compartment of the cartridge may be located upstream of the second air outlet of the second compartment of the cartridge.

As used herein, the terms 'nicotine source' and 'acid source' relate to substrates that are capable of releasing nicotine vapour and acid vapour respectively. Such vapours may be released by heating the respective nicotine source and acid source. The nicotine source and acid source may be separately formed and stored separately in the cartridge. The nicotine source, or the acid source, or both the nicotine source and the acid source may comprise one or more active ingredients that is configured to be released as a vapour during the vaporisation of nicotine and acid. The one or more active ingredients may comprise flavourings.

As used herein, the term 'air flow channel' relates to a conduit or a passage for an air stream. The air flow channel may be formed in any shape. For example, the air flow channel may be a straight channel, or it may have a sinusoidal or tortuous profile. The air flow channel may extend longitudinally along a length of the cartridge.

As used herein, the term "air inlet" is used to describe one or more apertures through which air streams may be drawn into the first compartment or the second compartment.

As used herein, the term "air outlet" is used to describe one or more apertures through which air streams may be drawn out of the first compartment or the second compartment.

Advantageously, the cartridge is configured such that the one or more air flow channels are arranged adjacent to, and in fluid communication with, their respective nicotine source and acid source. Therefore, an air stream may flow past, rather than through, the nicotine or acid sources. The passing air stream may collect vaporized nicotine, or vaporized acid, or both the vaporized nicotine and the vaporized acid as it passes through an air flow channel. The provision of air flow channels may reduce the resistance to draw (RTD) during use. This may advantageously result in a substantial increase in the volumetric flow rate in the air streams. This may promote the vaporization of nicotine or acid, and therefore the rate of aerosol generation may also increase accordingly. Advantageously, densely packed, or even non-permeable, nicotine or acid sources may be used since the air steam is not required to pass through the nicotine or acid sources.

The air flow channel may extend from either the air inlet, or the air outlet, and may extend longitudinally along only a portion of the compartment. For example, the air flow channel may extend from the air inlet and partially along the length of the compartment. As a result, the air stream may flow pass alongside an upstream portion of the nicotine or acid sources before flowing through the rest of the nicotine or acid source. The incoming air stream may initially flow through an upstream portion of the nicotine or acid source before flowing into the air flow channel, and subsequently flow alongside a downstream portion of the nicotine or acid source. Said air inlet, or air outlet, or both the air inlet and the air outlet may comprise one or more apertures to provide passage for an air stream to flow into or out of the cartridge. The first air inlet of the first compartment and the second air inlet of the second compartment may comprise the same or different numbers of apertures. The apertures may be identical, since identical apertures may advantageously simplify the manufacturing of said cartridge.

The flow area in each of the air flow channel may vary along the length of the flow channel. As used herein with reference to the invention, the term "flow area" is used to describe the cross-sectional area of an air inlet, or air outlet, or the air flow channel through which air stream flows. For example, the air flow channel may be narrower or wider at one end then another end, or it may be wider or narrower at a mid-section in comparison to either ends of the flow channel. Advantageously, the air flow channel may have a constant flow area along its length. This may allow a constant pressure drop along the length of the air flow channel.

The air flow channel may have any suitable cross-sectional shape. For example, the cross-sectional shape of the air flow channel may be circular, elliptical, square or rectangular. In one embodiment, the air flow channel has a substantially rectangular cross-sectional shape.

Only one of the two compartments may comprise an air flow channel. This may allow a desired air flow ratio between the two compartments, thus the desired reaction stoichiometry, to be achieved. For example, the compartment containing the acid source may be provided with an air flow channel, so as to encourage more acid vaporization in comparison to the corresponding nicotine vaporization, or vice versa.

Advantageously, the two compartments may each comprise an air flow channel. This may encourage more nicotine and acid vaporization in their respective compartments. Advantageously, the internal dimensions of the air flow channels in the two compartments may be different. This may allow a desired air flow ratio between the two compartments, thus a desired reaction stoichiometry, to be achieved. For example, the compartment containing the nicotine source may be provided with narrower air flow channels, or fewer air flow channels, so as to encourage more acid vaporization in comparison to the corresponding nicotine vaporization, or vice versa.

Advantageously, the acid source may comprise lactic acid. However, other acids that is suitable for forming a nicotine salt upon reacting with vaporized nicotine, such as pyruvic acid, may also be used as the acid source.

The first air flow channel may extend between the first air inlet and the first air outlet. The second air flow channel may extend between the second air inlet and the second air outlet. The first air flow channel may extend between the first air inlet and the first air outlet and the second air flow channel extend between the second air inlet and the second air outlet. The air flow channels may extend all the way through their respective compartments. This may advantageously allow the majority of air flow to pass over the entire lengths of the nicotine source or the acid source. As such, the resistance to draw (RTD) may be significantly reduced and the vaporization of nicotine or acid source increased. Such an arrangement may also allow a portion of the air flow to flow through the nicotine or acid sources. For example, a portion of air flow may diverge from an upstream position in the air flow channel into the nicotine or acid source, before reemerging into the air flow channel at a downstream position in the air flow channel.

Optionally, at least one of the first air flow channel and the second airflow channel extends along the length of the respective nicotine source or acid source. This may advantageously maximise vaporisation.

Optionally, at least one of the first air flow channel and the second airflow channel extends along a portion of the respective nicotine source or acid source. This may advantageously allow controlled exposure of the nicotine source or acid source to the passing air stream. Thus, it may be possible to control the ratio of vaporisation of nicotine and acid by varying the contacting surface area between the passing air stream and the respective nicotine and acid sources.

Optionally, at least one of the first air flow channel and the second air flow channel is at least partially defined by one or more protrusions extending from an interior wall of the respective first compartment or second compartment, wherein the one or more protrusions are configured to provide support for the nicotine source or the acid source. The one or more protrusions may be arranged so that some or all of the protrusions abut the nicotine source, or the acid source, or both the nicotine source and the acid source in their respective compartments. This may advantageously hold the nicotine source or the acid source, or both, in place. As a result the one or more protrusions may prevent the nicotine or acid source from blocking the air flow channel due to movement within the compartment. The one or more protrusions may be spaced apart from each other. The air flow channels may form between the one or more protrusions. The one or more protrusions may be spaced from the wall of the compartment. The air flow channels may be formed between the wall and the one or more protrusions.

Optionally, the one or more protrusions comprise ridges extending along the interior wall of the compartment, wherein at least one of the first air flow channel and the second air flow channel is formed between the ridges. The one or more ridges may comprise a plurality of ridges in parallel arrangement. This arrangement may advantageously provide multiple air flow channels along a longitudinal axis which may help maintain a low resistance to flow (RTD).

Optionally, the one or more protrusions form one or more tortuous air flow channels along the interior wall of the compartment. Such arrangement may lengthen the air flow path for a given cartridge length. Thus it may advantageously allow a longer residence time for the passing air flow and achieve a high concentration of nicotine or acid vapour at their respective air outlets.

Optionally, the one or more protrusions are a plurality of bosses on the interior wall of the first compartment or the second compartment. At least one of the first air flow channel and the second air flow channel may be formed between the bosses. Such arrangement may provide tortuous flow paths for the air stream. Thus it may improve vaporisation of nicotine or acid due to an increase in contact time and contact area with the air flow.

Optionally, the nicotine source comprises a first carrier material impregnated with nicotine. The amounts of nicotine recited herein may be the amount of nicotine base or the amount of ionised nicotine. Optionally, the first carrier material is impregnated with liquid nicotine or a solution of nicotine in an aqueous or non-aqueous solvent. Optionally, the first carrier material is impregnated with natural nicotine or synthetic nicotine. Optionally, the acid source comprises a second carrier material impregnated with lactic acid.

The first carrier material and the second carrier material may be the same or different, and may comprise one or more of glass, cellulose, ceramic, stainless steel, aluminium, polyethylene (PE), polypropylene, polyethylene terephthalate (PET), poly(cyclohexanedimethylene terephthalate) (PCT), polybutylene terephthalate (PBT), polytetrafluoroethylene (PTFE), expanded polytetrafluoroethylene (ePTFE), and BAREX®. Advantageously, the first carrier material and the second carrier material may comprise ceramic.

Optionally, the nicotine source comprises a porous ceramic impregnated with nicotine. The acid source may comprise a porous ceramic impregnated with acid. The nicotine source may comprise a first porous ceramic impregnated with nicotine. The acid source may comprise a second porous ceramic impregnated with acid. The porous ceramic materials may be able to maintain their shape regardless of the level of nicotine/acid impregnation. Therefore advantageously the flow area across each of the air flow channels may be consistent throughout the lifetime of the cartridge. Advantageously, the porous ceramic or porous ceramics may be formed from inert material, that does not react with the nicotine source or acid source.

The nicotine source may comprise an expandable foam material impregnated with nicotine. The acid source may comprise a foam material impregnated with acid. The nicotine source may comprise a first foam material impregnated with nicotine and the acid source comprise a second foam material impregnated with acid. Said foam material may be able to expand or shrink depending on the level of nicotine/acid impregnation. For example, the foam materials may shrink upon depletion of nicotine/acid source. This may advantageously causes the flow area across each of the air flow channels to expand. Therefore it may advantageously permit a higher air flow rate to encourage more nicotine or acid to vaporise. Advantageously, the foam materials may be expandable and thus provide a snug fit against the compartment walls.

Optionally, the first air flow channel and the second air flow channel may be arranged in parallel within the cartridge. As used herein, by "parallel" it is meant that the first compartment and the second compartment are arranged within the cartridge so that in use a first air stream drawn through the cartridge passes into the first compartment through the first air inlet, downstream through the first compartment and out of the first compartment through the first air outlet and a second air stream drawn through the cartridge passes into the second compartment through the second air inlet, downstream through the second compartment and out of the second compartment through the second air outlet. This arrangement may allow the nicotine and acid to vaporized from their respective sources separately and simultaneously, before reacting with each other downstream to form an aerosol with nicotine salt.

Optionally, at least one of the nicotine source and the acid source is partitioned from the respective first air flow channel and the second air flow channel by one or more mesh heating elements. Each of the one or more mesh heating elements may comprise one or more openings through which fluid can pass. The one or more mesh heating elements may advantageously abut and be supported by one or more protrusions extending from the interior walls of the first or second compartment. The one or more mesh heating elements may form the one or more protrusions, and may keep the nicotine/acid source in place in the compartment. The openings in the mesh heating elements may allow air flow in the air flow passage to pass through, and interact with, the nicotine/acid source. The openings may advantageously create turbulence in the passing air stream in the air flow passage, which may lengthen the interaction between the air stream and the nicotine and acid sources. The openings may be sized to provide passage for vapour but prevent liquid from passing through. This may reduce or eliminate entrainment of liquid nicotine source or liquid acid source into the air passing through the air flow channels.

The heater may be configured to heat the first compartment and the second compartment of the cartridge to a temperature of below about 250 degrees Celsius. Preferably, the heater is configured to heat the first compartment and the second compartment of the cartridge to a temperature of between about 80 degrees Celsius and about 150 degrees Celsius.

The heater may be configured to heat the first compartment and the second compartment of the cartridge to substantially the same temperature.

As used herein with reference to the invention, by "substantially the same temperature" it is meant that the difference in temperature between the first compartment and the second compartment of the cartridge measured at corresponding locations relative to the heater is less than about 3° C.

Optionally, the one or more mesh heating elements comprise one or more susceptors configured to heat at least one of the nicotine source and the acid source when exposed to an eddy current induced by an inductive heater. The inductive heater may be an inductor coil provided in the aerosol generating system which generates a changing magnetic flux across the one or more susceptors. This induces eddy currents in the one or more susceptors that generate heat. The mesh heating element may advantageously be disposable with the cartridge. The susceptor may be a piece or pieces of the one or more mesh heating elements. The susceptor may be a ferrous susceptor. Identical susceptors may be provided for both of the first compartment and the second compartment. During inductive heating both of the susceptors may be subjected to the same changing magnetic flux. Different susceptor arrangements may be provided for the nicotine source and the acid source, which may allow different heating temperatures to be achieved in their respective compartments. For example, the first and second compartments may each be provided with a suspector with a different design or material.

Optionally, the cartridge comprises a cavity located between the first compartment and the second compartment for receiving a heater configured to heat the first compartment and the second compartment. The heater may be provided as part of the aerosol-generating device and arranged to be inserted into the cavity of the cartridge during use. The heater may be arranged to heat both the nicotine source and the acid source simultaneously, or two heaters may be provided to heat the two compartments separately. The heater may comprise a resistive heating element. The cavity may be located at the centre of the cartridge. The cavity may be equidistant between the nicotine source and the acid source. The cavity may be arranged offset from the centre of the cartridge, and may be positioned closer to one of the nicotine source and the acid source. This may allow the nicotine source and the acid source to be heated to a different temperature during use.

In use, heating the first compartment and the second compartment of the cartridge to a temperature above ambient temperature may enable the vapour concentrations of the nicotine in the first compartment of the cartridge and the vapour pressure of lactic acid in the second compartment of the cartridge to be controlled and balanced proportionally to yield an efficient reaction stoichiometry between the nicotine and the lactic acid. This may improve the efficiency of the formation of nicotine lactate salt particles and the consistency of delivery to a user. It may also reduce the delivery of unreacted nicotine and unreacted lactic acid to a user.

Optionally, the flow area of the first air inlet is different to the flow area of the second air inlet. This may allow ma greater rate of vaporisation at one of the nicotine source and the acid source compared to the other. Optionally, the first air inlet of the first compartment comprises a larger number of identical apertures than the second air inlet of the second compartment. Optionally, the flow area of the first air inlet is smaller than the flow area of the second air inlet. This may allow a greater rate of vaporisation of the acid source. Optionally, the ratio of flow area of the first air inlet to the flow area of the second air inlet is arranged to be between about 3:4 and about 1:2. Optionally, the flow area of the first air inlet is between about 0.1 square millimetres and about 1.6 square millimetres and the flow area of the second air inlet is between about 0.2 square millimetres and about 2.4 square millimetres. These arrangements may advantageously provide an optimal ratio of nicotine and acid vapours.

Optionally, prior to first use of the cartridge, one or both of the air inlets and the air outlets may be sealed by one or more removable or frangible barriers. For example, one or both of the first air inlet of the first compartment and the second air inlet of the second compartment may be sealed by one or more peel-off or pierceable seals. The one or more removable or frangible barriers may be formed from any suitable material. For example, the one or more removable or frangible barriers may be formed from a metal foil or film.

Optionally, the cartridge comprises a third compartment downstream of both of the first compartment and the second compartment. The third compartment may be in fluid communication with the first air outlet of the first compartment and the second air outlet of the second compartment. The nicotine vapour in the first air stream may react with the lactic acid vapour in the second air stream in the third compartment to form an aerosol of nicotine lactate salt particles. Optionally, the third compartment comprises an aerosol outlet in fluid communication with the mouthpiece. Optionally, the third compartment comprises one or more aerosol-modifying agents. For example, the third compartment may comprise one or more sorbents, one or more flavourants, one or more chemesthetic agents or a combination thereof.

Optionally, the cartridge comprises a body portion and one or more end caps. Optionally, the cartridge comprises a body portion and a distal end cap. Optionally, the cartridge comprises a body portion and a proximal end cap. Optionally, the cartridge comprises a body portion, distal end cap and a distal end cap.

Optionally, one or more apertures forming the first air inlet of the first compartment of the cartridge and one or more apertures forming the second air inlet of the second compartment of the cartridge are provided in the distal end cap.

Optionally, one or more apertures forming the first air outlet of the first compartment of the cartridge and one or more apertures forming the second air outlet of the second compartment of the cartridge are provided in the proximal end cap.

Optionally, some or all of the one or more protrusions that define the air flow channels are provided on the distal end cap, or the proximal end cap, or both the distal end cap and the proximal end cap.

Optionally, the cartridge is formed from one or more materials that are nicotine-resistant and acid-resistant. Optionally, the first compartment of the cartridge is coated with one or more nicotine-resistant materials and the second compartment of the cartridge is coated with one or more acid-resistant materials. Examples of suitable nicotine-resistant materials and acid-resistant materials include, but are not limited to, polyethylene (PE), polypropylene (PP), polystyrene (PS), fluorinated ethylene propylene (FEP), polytetrafluoroethylene (PTFE), epoxy resins, polyurethane resins, vinyl resins, liquid crystal polymers (LCP) and modified LCPs, such as LCPs with graphite or glass fibres. The use of one or more nicotine-resistant materials may enhance the shelf life of the cartridge.

Optionally, the cartridge is formed from one or more thermally conductive materials. Optionally, at least one of the first compartment of the cartridge and the second compartment of the cartridge are coated with one or more thermally conductive materials. The use of one or more thermally conductive materials may advantageously increase heat transfer from a heating element to the nicotine source or the lactic acid source. Suitable thermally conductive materials include, but are not limited to, metals such as, for example, aluminium, chromium, copper, gold, iron, nickel and silver, alloys, such as brass and steel and combinations thereof.

The cartridge may be formed by any suitable method. Suitable methods include, but are not limited to, deep drawing, injection moulding, blistering, blow forming and extrusion.

The cartridge may be designed to be disposed of once the nicotine in the first compartment or the lactic acid in the second compartment are depleted.

The cartridge may be designed to be refillable.

According to an aspect of the present invention there is provided an aerosol-generating system comprising a cartridge as described herein; and an aerosol-generating device comprising a housing defining a cavity for receiving at least a portion of the cartridge; and a heater for heating at least one of the first compartment and the second compartment of the cartridge.

The aerosol-generating system may further comprise a mouthpiece. In such embodiments, nicotine vapour released from the nicotine source in the first compartment of the cartridge and lactic acid vapour released from the lactic acid source in the second compartment of the cartridge may react with one another in the gas phase in the mouthpiece to form an aerosol of nicotine lactate salt particles.

The mouthpiece may be configured for engagement with the cartridge.

Optionally, the mouthpiece is configured for engagement with the cartridge, the combination of the cartridge and the mouthpiece may simulate the shape and dimensions of a combustible smoking article, such as a cigarette, a cigar, or a cigarillo. In such embodiments the combination of the cartridge and the mouthpiece may simulate the shape and dimensions of a cigarette.

The mouthpiece may be configured for engagement with the housing of the aerosol-generating device.

The mouthpiece may be designed to be disposed of once the nicotine in the first compartment and the lactic acid in the second compartment are depleted.

The mouthpiece may be designed to be reusable. In embodiments in which the mouthpiece is designed to be reusable, the mouthpiece may advantageously be configured to be removably attached to the cartridge or the housing of the aerosol-generating device.

Optionally, the aerosol-generating system comprises a consumable cartridge according to the invention and a reusable aerosol-generating device comprising a heater for heating at least one of the first compartment and the second compartment of the cartridge.

The heater may be an electrical heater. The heater may be a resistive heater.

The heater may be arranged to circumscribe at least a portion of the cartridge when the cartridge is received within the cavity.

Optionally, the heater is located within the cavity of the aerosol-generating device and the cartridge may comprise a cavity for receiving the heater as described above. In such embodiments, the heater of the aerosol-generating device may advantageously be an elongate heater in the form of a heater blade. The heater blade may have a width that is greater than its thickness. The cavity in the cartridge may be configured as an elongate slot.

Optionally, the heater is an inductive heater and the cartridge may comprise a susceptor for heating the first compartment and the second compartment of the cartridge as described above.

The aerosol-generating system may further comprise a power supply for supplying power to the heater and a controller configured to control a supply of power from the power supply to the heater.

The aerosol-generating device may comprise one or more temperature sensors configured to sense the temperature of the heater and the temperature of the first compartment and the second compartment of the cartridge. In such embodiments, the controller may be configured to control a supply of power to the heater based on the sensed temperature.

Optionally, the aerosol-generating device comprises a user input device. The user input device may comprise at least one of a push-button, a scroll-wheel, a touch-button, a touch-screen, and a microphone. The user input device may allow a user to control one or more aspects of the operation of the aerosol-generating device. The user input device may allow a user to activate a supply of electrical power to the heater, to deactivate a supply of electrical power to the heater, or both.

The power supply may be any suitable power supply, for example a DC voltage source such as a battery. The power supply may be a Lithium-ion battery, a Nickel-metal hydride battery, a Nickel cadmium battery, or a Lithium based battery, for example a Lithium-Cobalt, a Lithium-Iron-Phosphate, Lithium Titanate or a Lithium-Polymer battery.

The power supply may include a rechargeable lithium ion battery. The electrical power supply may comprise another form of charge storage device such as a capacitor. The electrical power supply may require recharging. The electrical power supply may have a capacity that allows for the storage of enough energy for one or more uses of the aerosol-generating device. For example, the electrical power supply may have sufficient capacity to allow for the continuous generation of aerosol for a period of around six minutes, corresponding to the typical time taken to smoke a conventional cigarette, or for a period that is a multiple of six minutes. In another example, the electrical power supply may have sufficient capacity to allow for a predetermined number of puffs or discrete activations.

The controller may be configured to commence a supply of electrical power from the electrical power supply to the heater at the start of a heating cycle. The controller may be configured to terminate a supply of electrical power from the electrical power supply to the heater at the end of a heating cycle.

The controller may be configured to provide a continuous supply of electrical power from the electrical power supply to the heater.

The controller may be configured to provide an intermittent supply of electrical power from the electrical power supply to the heater. The controller may be configured to provide a pulsed supply of electrical power from the electrical power supply to the heater. A pulsed supply of electrical power to the heater may facilitate control of the total output from the heater during a time period. Controlling a total output from the heater during a time period may facilitate control of temperature.

The controller may be configured to vary the supply of electrical power from the electrical power supply to the heater. The controller may be configured to vary a duty cycle of the pulsed supply of electrical power. The controller may be configured to vary at least one of a pulse width and a period of the duty cycle.

For the avoidance of doubt, features described above in relation to one aspect of the invention may also be applicable to other aspects of the invention. In particular, features described above in relation to the cartridge of the invention may also relate, where appropriate, to the aerosol-generating systems of the invention, and vice versa.

Embodiments of the invention will now be described, by way of example only, with reference to the accompanying drawings, in which:

FIGS. 7a and 7b are sectional side view of cartridges according to different embodiments of the present invention;

Figure 1:
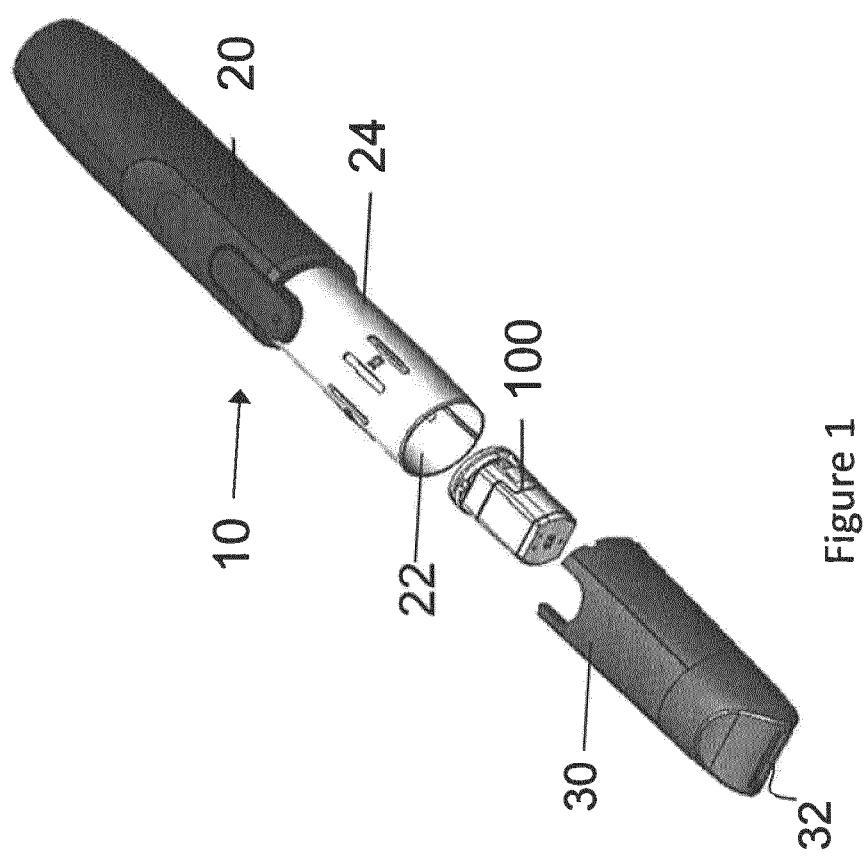
FIG. 1 is a perspective view of an aerosol-generating system according to an embodiment of the present invention.
Figure 2:
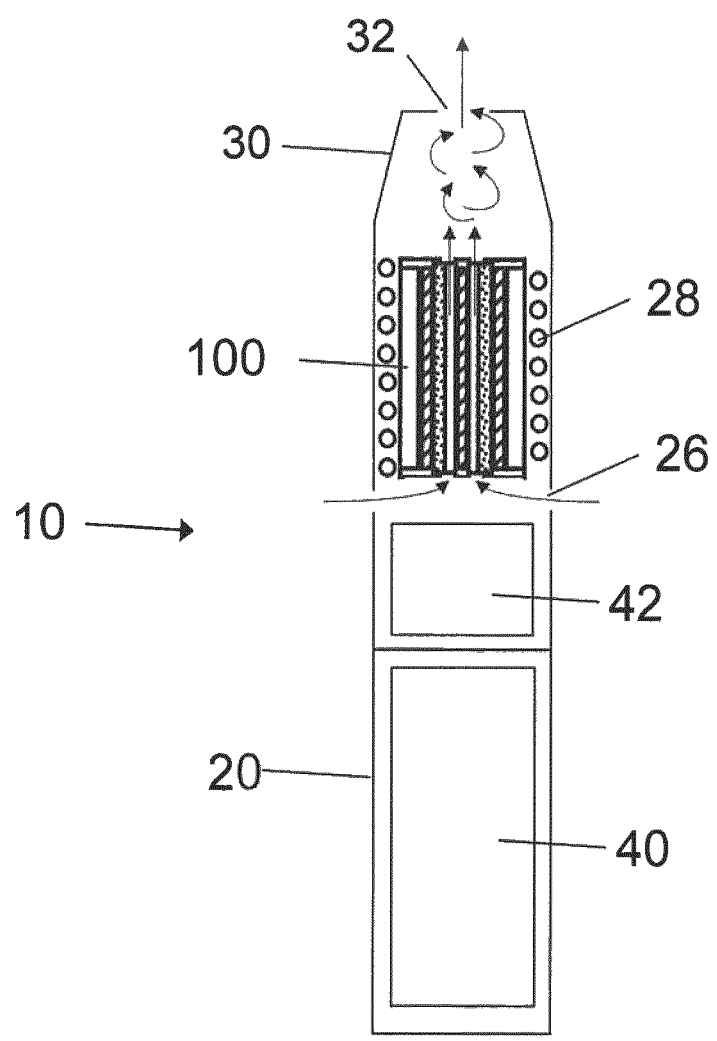
FIG. 2 is a sectional view of the aerosol-generating system of FIG. 1.

FIGS. 1 and 2 show an aerosol-generating system 10 comprising an aerosol-generating device 20 and a cartridge 100 for use with the aerosol-generating device 20. The aerosol-generating system further comprising a mouthpiece 30 configured to attach releasably to a proximal end 24 of the aerosol-generating device 20.

The aerosol-generating device 20 comprises a housing having a cavity 22 for receiving the cartridge 100 through an opening at the proximal end 24 of the housing. The aerosol-generating device 20 comprises an inductor coil 28 within the cavity 22. The inductor coil is held within the internal walls the cavity 22 as shown in FIG. 2.

The aerosol-generating device 20 comprises an electrical energy supply 40 in the housing, in this example a rechargeable lithium ion battery. The device 10 further comprises a controller 42 connected to the battery 30, the inductor coil 28 and a user interface (not shown). In this embodiment, the user interface comprises a mechanical button. Upon activating the user interface, the controller supplies the inductor coil 28 with a high frequency oscillating current, to produce an oscillating magnetic field. This causes one or more susceptors in the cartridge 100 to heat as a result of induced eddy currents and hysteresis losses. This heats the nicotine source and a lactic acid source contained within the cartridge, producing a nicotine vapour and a lactic acid vapour. As the user puffs on the mouthpiece 30, a flow of air is drawn from an air inlet 26 through the cartridge to convey the vaporized nicotine and lactic acid towards the mouthpiece. The vaporized nicotine and lactic acid, each in a gas phase, then react and cool in the mouthpiece 30 to form an aerosol containing nicotine salt particles. During the puff, the user receives a volume of the aerosol through an exhaust outlet 32.

Figure 3:
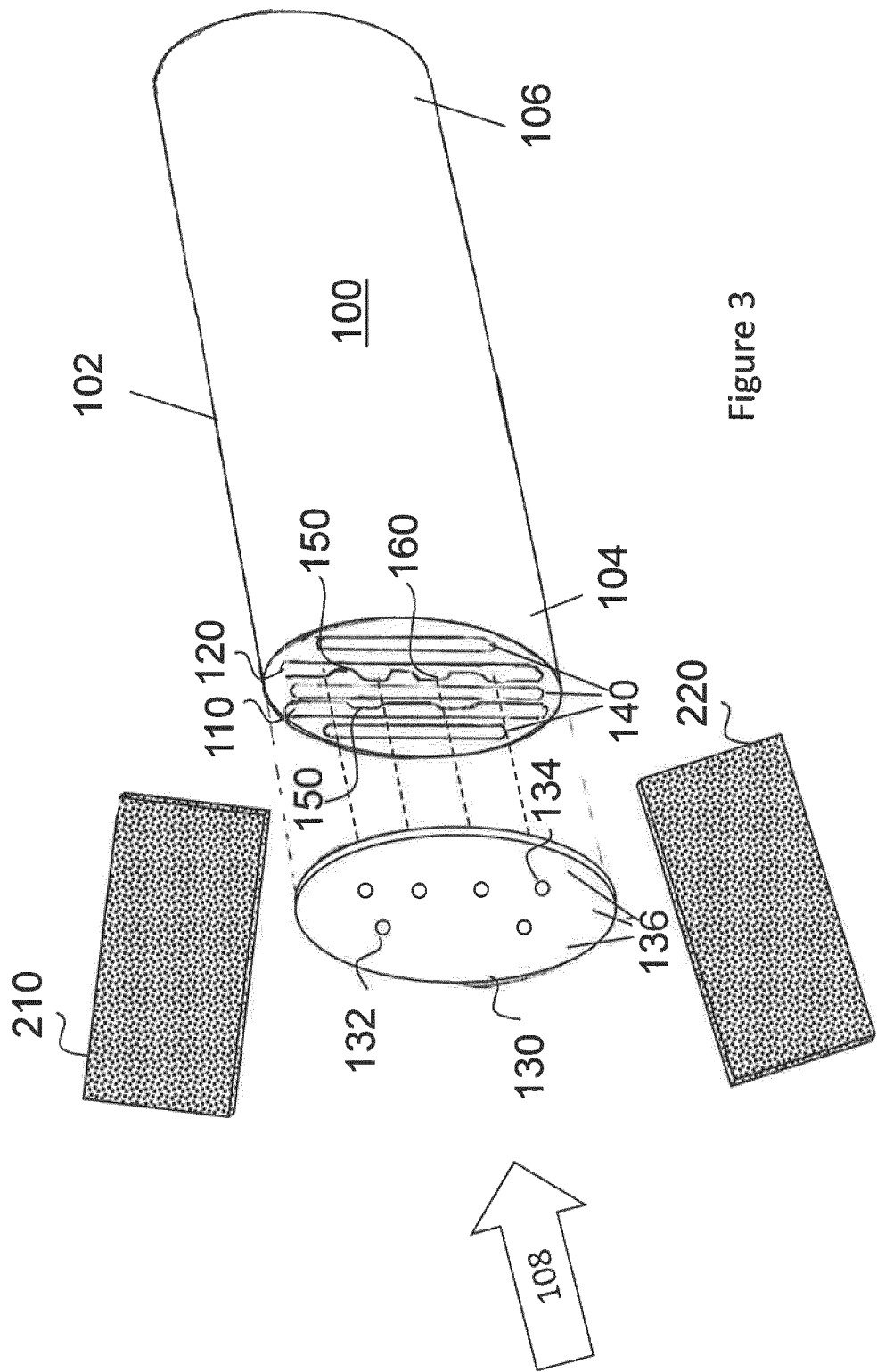
FIG. 3 is an exploded perspective view of a cartridge in the aerosol-generating system of FIG. 1.

FIG. 3 is an exploded view of the cartridge 100. The cartridge 100 has a length of about 15 millimetres, a width of about 7.1 millimetres and a height of about 6.75 millimetres. The cartridge 100 in this illustrated example comprises an elongate cartridge body 102 closed by an end cap 130 at either of its distal 104 and proximal ends 106. The body 102 has a length of about 11 millimetres, a width of about 7.1 millimetres and a height of about 6.75 millimetres. The end cap 130 has a length of about 2 millimetres, a width of about 7.1 millimetres and a height of about 6.75 millimetres. The cartridge 100 comprises a nicotine source 210 contained in a first compartment 110 and a lactic acid source 220 contained in a second compartment 120 of the cartridge 100. The first compartment 110 and the second compartment 120 each extend longitudinally within the cartridge body 102. The first compartment 110 and the second compartment 120 are arranged to be closed by an end cap 130 at their respective distal end 104 and proximal end 106. The first compartment 110 and the second compartment 120 are identical compartments each having a substantially rectangular cross-section with a depth of about 1 mm.

The first compartment 110 and the second compartment 120 are arranged in a parallel configuration. The incoming air stream splits before entering the first compartment 110 and the second compartment 120. The nicotine vapour and the lactic acid vapour are generated simultaneously in separate compartments.

The distal end cap 130 comprises a plurality of air inlets 132, 134 providing flow passages between an incoming air flow 108 and the first and second compartments 110, 120. The air inlets are identical apertures through the distal end cap. The plurality of air inlets 132, 134 comprise first air inlets 132 in fluid communication with the first compartment 110, and second air inlets 134 in fluid communication with the second compartment 134. In the illustrated example, there are more second air inlets 134 than first air inlets 132. This results in a larger cross-sectional flow area through the second air inlets 134 than through the first air inlets 132. This enables a higher volumetric air flow through the second compartment 120 than the first compartment 110. This causes more acid to vaporize in the second compartment 120 than would be the case if there were fewer second air inlets.

The end cap 130 as shown in FIG. 3 is a distal end cap having air inlets 132, 134 opened to the first and second compartments 110, 120. In this example, a proximal end cap, comprising air outlets (not shown) that mirror the air inlets 132,134 at the distal end cap, is provided at the proximal end 106 of the cartridge 100. The air outlets at the proximal end cap are in fluid communication with the first and second compartments 110, 120, as well as the exhaust 32 at the mouthpiece 30. The first compartment 110 and the second compartment 120 each extends from the distal end cap to the proximal end cap. That is, the first compartment 110 and the second compartment 120 both extend all the way through the length of the cartridge body 102.

The cartridge body 102 comprises a plurality of heater cavities 140 each extending along the longitudinal axis of the cartridge 100. Each of the heater cavities has a depth of 0.4 millimetres. The heater cavities 104 are parallel to the first compartment 110 and the second compartment 120. Each of the heater cavities 140 and its corresponding first compartment 110 or second compartment 120 are separated by 0.4 millimetres. Each of the plurality of heater cavities 140 is arranged to receive a susceptor. The plurality of heater cavities 140 are closed at both of the distal end 104 and the proximal end 106 by their respective distal end cap and proximal end cap. In the illustrated example, each of the first compartment 110 and the second compartment 120 is sandwiched between a pair of heater cavities 140. In this embodiment, a plurality of identical susceptors are used, one placed in each heater cavity 140. During use both the nicotine source 210 and the acid source 220 are heated to the same temperature.

The first compartment 110 and the second compartment 120 each comprise a plurality of parallel ridges 150 extending longitudinally along the length of the cartridge 100. The plurality of ridges 150 protrude from a sidewall of the first compartment 110 and a sidewall of the second compartment 120. Once assembled, the nicotine source 210 and the lactic acid source 220 abut the plurality of ridges 150 of the cartridge. This is illustrated in the sectional view of the cartridge 100 in FIG. 4. Once the nicotine source 210 and the lactic acid source 220 are assembled into the first compartment 110 and the second compartment 120, they rest against the ridges 150. The sources 210, 220 are closed by the end caps 130 at either ends of the cartridge 100 and in fluid communication with their respective air inlets 132, 134 and air outlets 133,135.

Figure 4:
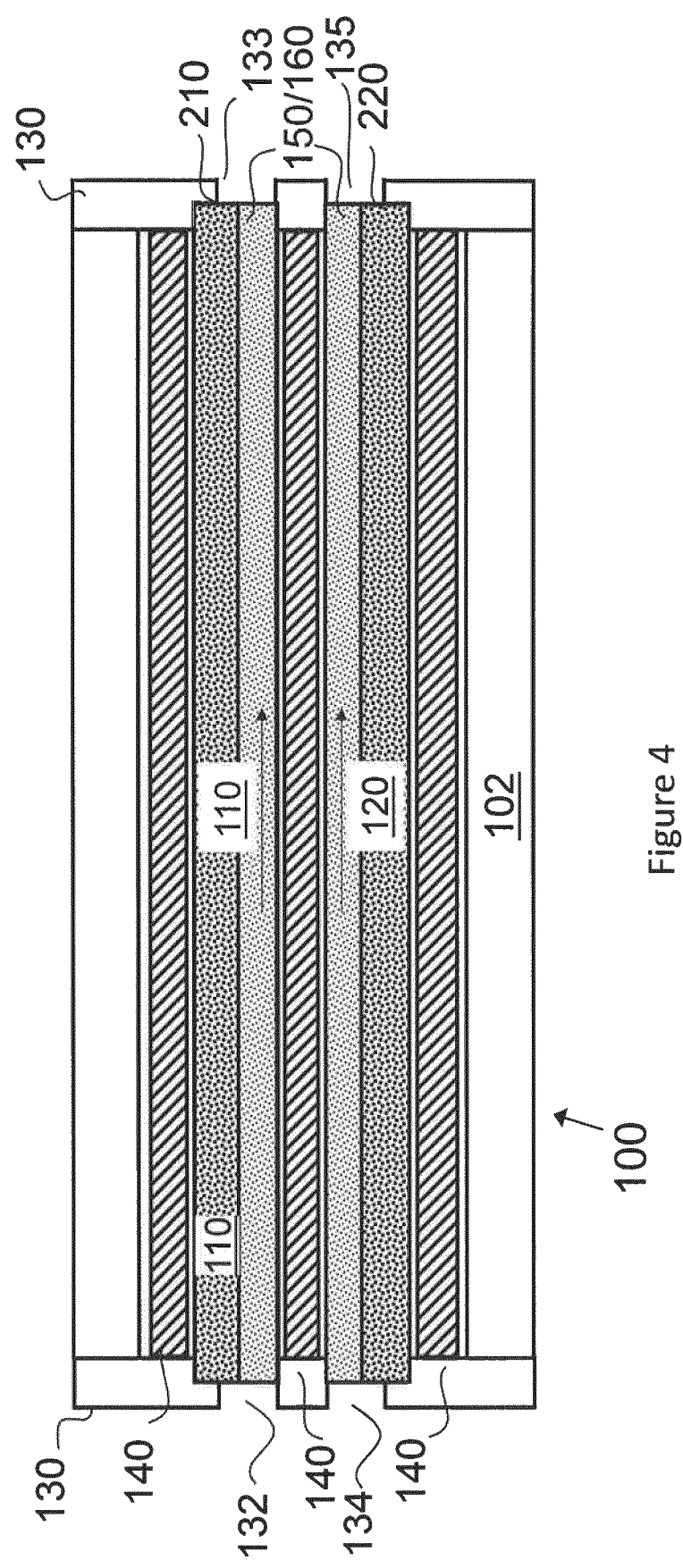
FIG. 4 is a first sectional view of the cartridge of FIG. 1.
Figure 5:
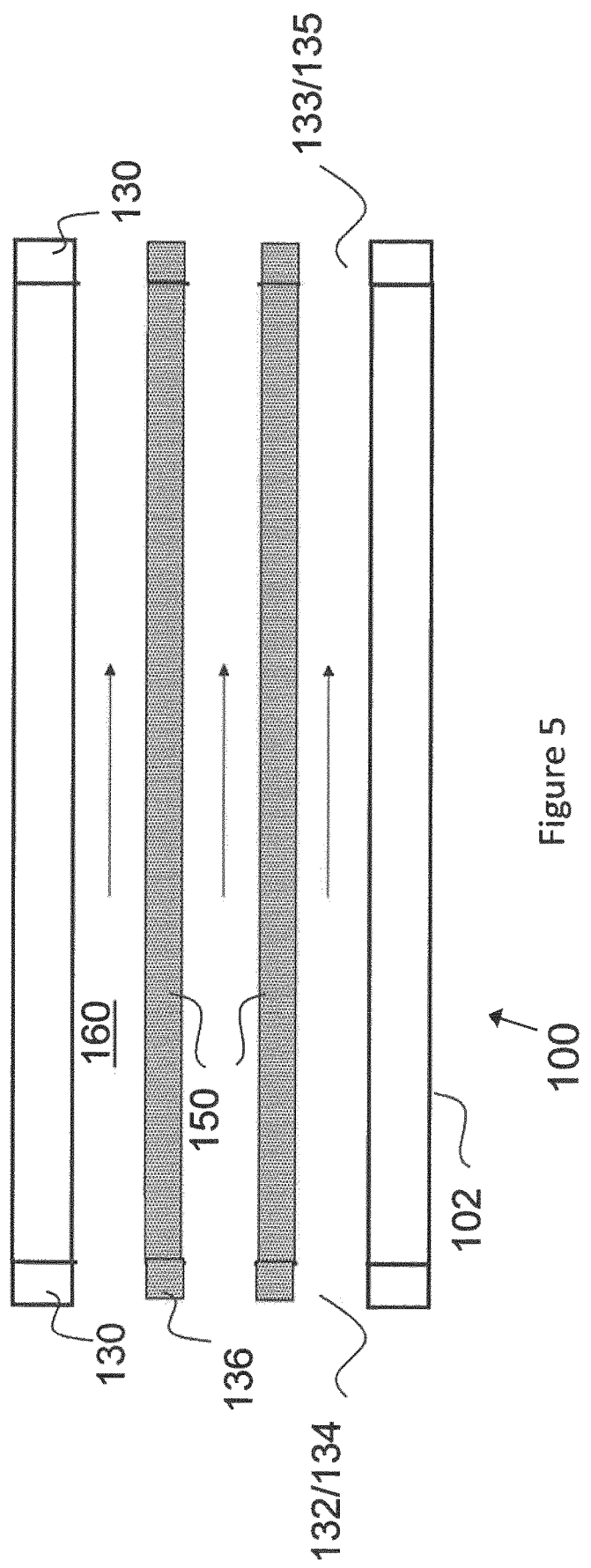
FIG. 5 is a second sectional view of the cartridge of FIG. 1, orthogonal to the view of FIG. 4.

FIG. 5 is a different sectional view of the cartridge 100, orthogonal to the section of FIG. 4, showing the flow path of air streams flowing through the interior of the cartridge 100. The air streams enter the cartridge 100 through air inlets 132,134 and exit the cartridge 100 through air outlets 133,135. Both the air inlets 132,134 and the air outlets 133,135 are provided in the end caps 130. A plurality of air flow channels 160 are formed within the voids between the parallel ridges 150, the nicotine/lactic acid source and the side walls of the cartridge 100. As the air streams pass through the air flow channels 160, they collects vaporized nicotine and lactic acid at the surface of the respective nicotine source 210 and lactic acid source 220.

In this example, the nicotine source 210 comprises a porous ceramic substrate impregnated with a nicotine liquid. The lactic acid source 220 comprises a porous ceramic impregnated with lactic acid. The nicotine liquid also comprises flavorings that are arranged to vaporize with the nicotine when the nicotine source is heated. Said flavorings are arranged to produce a desirable taste in the generated aerosol. More specifically, the nicotine source 210 comprises a porous ceramic substrate impregnated with about 10 milligrams of nicotine and about 4 milligrams of menthol, and the lactic acid source 220 comprises a porous ceramic substrate impregnated with about 20 milligrams of lactic acid.

The porous ceramic is a relatively inert material that does not deteriorate when it is put in contact with either the nicotine liquid or the lactic acid. The rigidity of the porous ceramic ensures consistent external dimensions for both of the nicotine and lactic acid sources 210, 220 over the lifetime of the cartridge. More specifically, the nicotine and lactic sources 210, 220 do not expand or shrink dependent on the amount of liquid remaining. The cross sectional area of the air flow channels 150 remains unchanged during different stages of cartridge use, thus providing a consistent puffing experience for the user.

In practice, the user puffs on the mouthpiece 30 to draw a volume of air flow through the air flow channels 150. A portion of the air stream entering the first compartment 110 and the second compartment 120 may penetrate beneath the surface of the porous ceramic material, before emerging back to the air flow channels 160. This aids the evacuation of vaporized nicotine and lactic acid as it is generated from within the pores of the ceramic.

Figure 6:
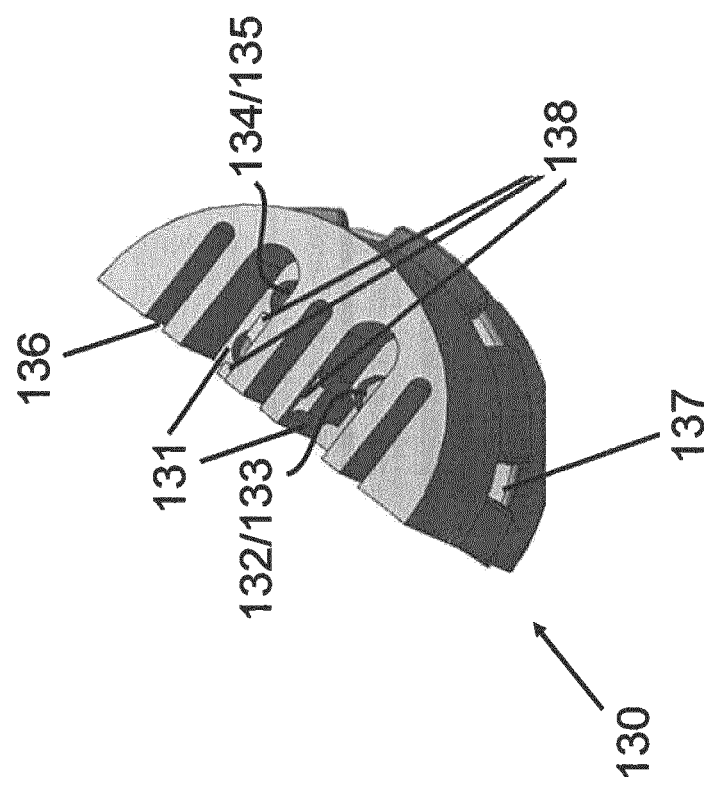
FIG. 6 is a perspective view of an end cap as fitted to the cartridge of FIG. 3.

As shown in FIG. 5, each of the end caps 130 comprises end cap ridges 138 which are complementary to the ridges 150 in the cartridge 100. The inwardly facing side of the end cap 130 is shown in further detail in the perspective view of FIG. 6. The end cap 130 shown in FIG. 6 is a distal end cap configured to close the distal end 104 of the cartridge body 102. The proximal end cap is of a similar design where the air inlets arrangement is mirrored for closing the proximal end 106 of the cartridge body 102. The end cap 130 comprises fittings 137 for effecting a non-releasable coupling with the cartridge body 102. This ensures the user cannot dismantle or tamper with the cartridge 100.

The end cap 130 comprises a plurality of end cap cavities 131 each complementary to the first compartment 110 and second compartment 120 in the cartridge body 102. The end cap cavities 131 are arranged to open on an inwardly-facing surface and extend partially along the depth of the end cap 130. The end cap cavities 1371 are configured to contain the ends of both the nicotine source 210 and the lactic acid source 220 when the end cap 130 is fitted onto the distal end 104 or the proximal end 106 of the cartridge body 102.

The plurality of end cap ridges 138 are complementary to the plurality of ridges 150 in the first compartment 110 and the second compartment 120, and providing further support to the nicotine and lactic acid sources 210,220. The end cap ridges 138 also serve as extension to the air flow channels 160. By positioning the end cap cavities 137 over the nicotine and lactic acid sources 210,220 in the first and second compartments 110,120, the end caps can be easily aligned and assembled onto the cartridge body 102.

The end cap 130 further comprises end cap heater cavities 136 complementary to the heater cavities 140 in the cartridge body 102. Similar to the end cap cavities 137, the end cap heater cavities 136 open at an inwardly-facing surface of the cartridge body 102 and extend partially along the depth of the end cap 130. The end cap heater cavities 136 allow the susceptors as contained in the heater cavities to be further supported therein. In this particular embodiment, the end cap heater cavities 136 are configured to provide a snug fit to the susceptors. As a result, the susceptors are held firmly in place by the end caps.

As discussed with reference to FIG. 5, the parallel ridges 150 protruding from the cartridge wall serve several functions. They support and stabilize the nicotine and lactic acid sources when they are assembled into their respective first and second compartments 110,120. The ridges 150 also form air channels 160 to allow air streams to pass over the surface of the nicotine and lactic acid sources 110, 120 to evacuate vaporized nicotine and lactic acid effectively. Because the majority of the air stream does not flow through the nicotine or lactic acid sources, this arrangement significantly reduces the resistance to draw (RTD).

The ridges 150 as shown in FIG. 5 define straight flow paths and therefore they allow vaporized nicotine and lactic acid to be promptly evacuated from their respective first and second compartments 110,120. However in some cases, other types of protrusions may be used in place of the ridges 150 to provide other functions. For example, instead of straight ridges, ridges with a sinusoidal profile may be used to induce turbulence in the air streams. This improves convection within the air flow channels, as well as forcing a larger portion of the air stream to penetrate beneath the surface of the porous nicotine and lactic acid source.

FIG. 7a shows a sectional side view of an alternative cartridge design having a plurality of bosses 152 extending from the side walls of the compartments. In this embodiment, the bosses replace the parallel ridges 150 as shown in FIG. 5. These bosses 152 support and stabilize the nicotine and lactic acid sources 210,220 once they are assembled into their respective compartments 110,120. As illustrated in FIG. 7a, the bosses result in tortuous flow paths in the air streams. This induces more turbulence in the air flow, and so increases the contact time and contact area of the air with the nicotine source and acid source.

In an alternative embodiment, as shown in FIG. 7b, the end cap 130 as shown in FIG. 6 is used for closing a cartridge body 102c that does not feature any ridge in either the first compartment 110 or the second compartment 120. Therefore, a single air flow channel 160c is formed in the void between the surface of the sources 210, 220 and the sidewalls of the compartments 110,120. In this embodiment, the nicotine source 210 and the lactic acid source 220 are retained in the respective first 110 and second 120 compartments solely by the end cap ridges 138. In use, air streams entering the first and second compartments 110,120 may flow freely across the width of a single air flow channel 160c. This encourages lateral convection across each of the compartments 110,120.

Figure 8:
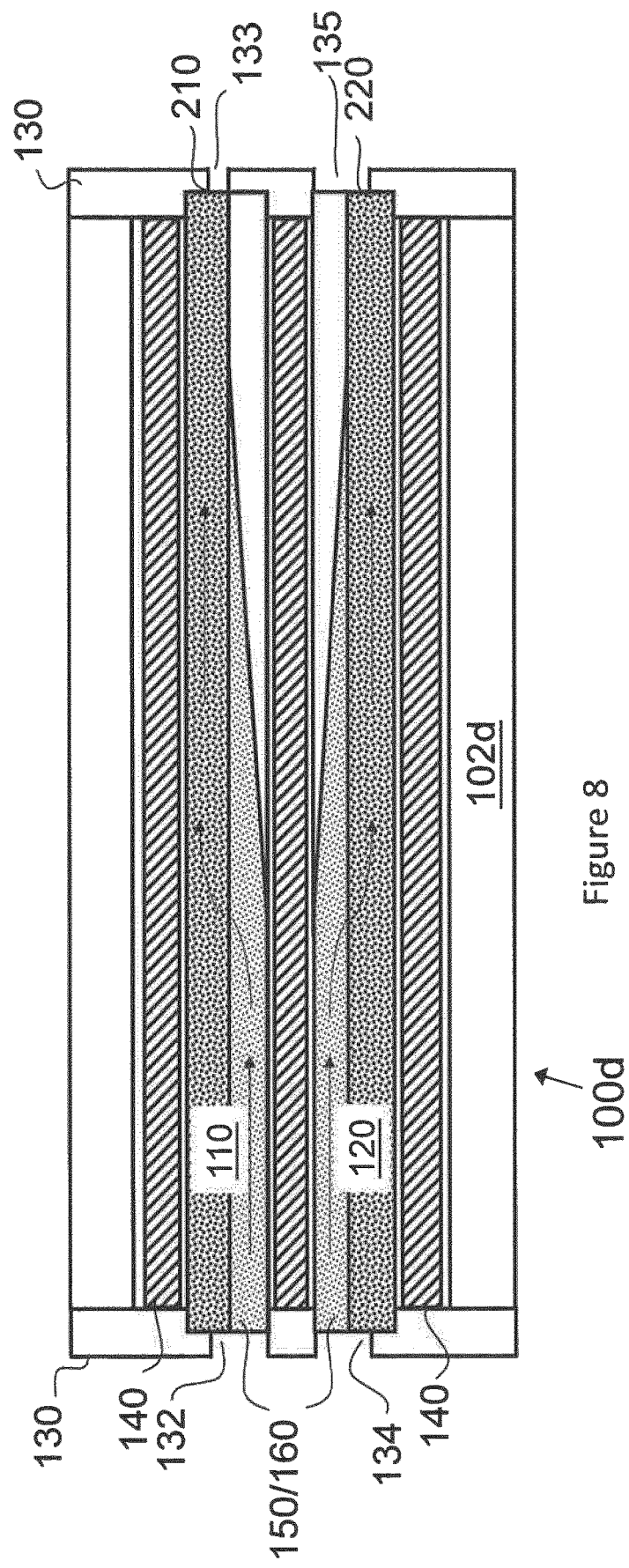
FIG. 8 is a sectional side view of a cartridge according to another embodiment of the present invention.

In an alternative embodiment, the airflow channels 160 do not extend all the way through the cartridge body 102d. As shown in FIG. 8, the channels between the ridges 150 gradually fill towards the air outlets 133,135. This causes the cross-sectional area across each of the air flow channels 160 to progressively reduce in the direction of air flow. In the illustrated example, the air flow channels 160 do not open to the air outlets 133,135 at the proximal end 106 of the cartridge 100d. Instead, the air streams in the air flow channels are forced to penetrate and flow through the nicotine and lactic acid sources 210,220, before exiting the cartridge 100d through the air outlets 133,135. This means that the air streams in the air flow channels, already dosed with nicotine and lactic acid vapors, are exposed to more vaporized nicotine and lactic acid within the pores of the porous ceramic material.

In another embodiment, the heater cavities 140 in the cartridge 100 are merged with their respective first compartment 110 and second compartment 120. More specifically, the susceptors are no longer supported in separate heater cavities 140. Instead they are held in place by the end cap heater cavities 136. As a result, the susceptors no longer conduct heat through the sidewalls of the compartments 110,120. Instead, the susceptors directly heat the nicotine source 210 and lactic source 220 in their respective compartments 110,120. The susceptors in this case are mesh susceptors. The use of mesh susceptors permits unrestricted air flow within the compartments, and thus enhances heat convection therein.

Figure 9:
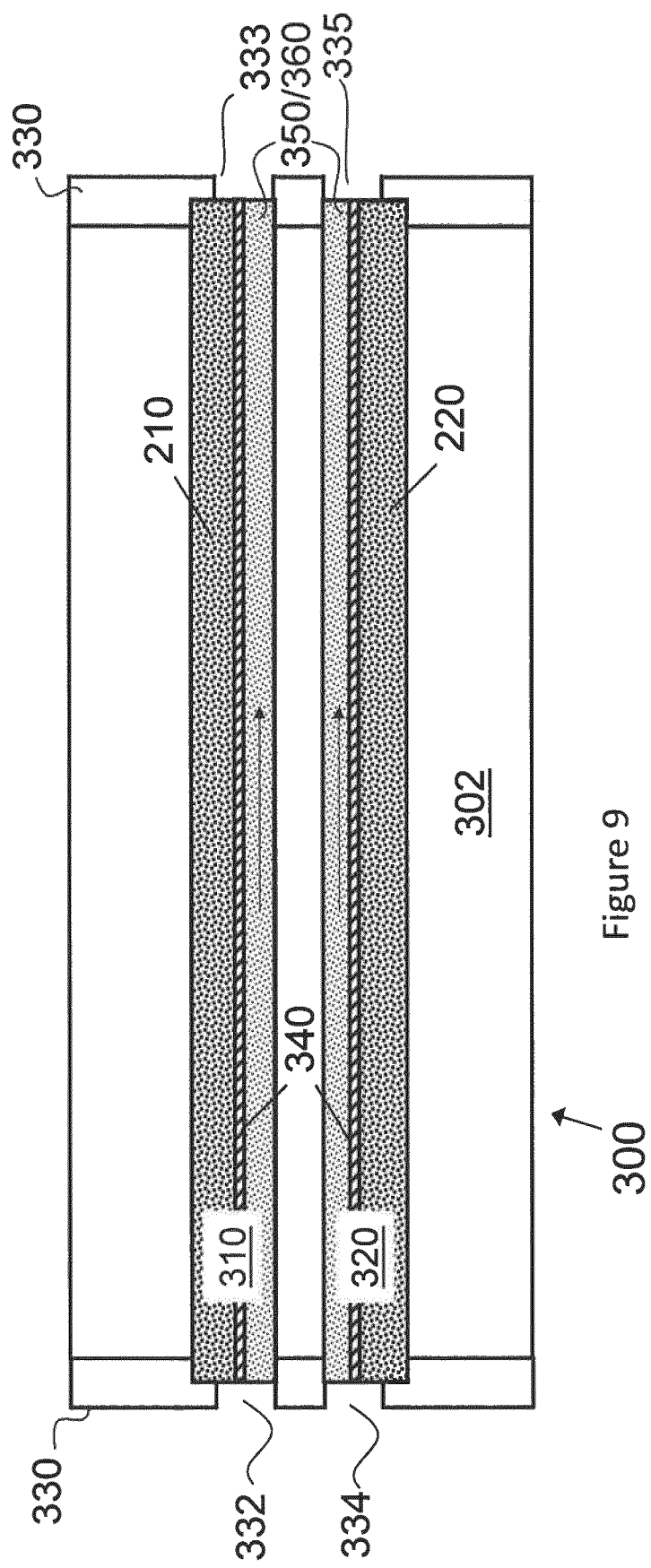
FIG. 9 is a sectional side view of a cartridge according to yet another embodiment of the present invention.

FIG. 9 shows a cartridge 300 according to an alternative embodiment. The cartridge 300 is closed by end caps 330 at either end of the cartridge 300. In comparison with the cartridge 100 as shown in FIG. 4, the cartridge 300 employs susceptors 340 that are put into direct contact with the nicotine and lactic acid sources 210,220. The susceptors in cartridge 300 are ferrous meshes. The mesh susceptors are arranged to be positioned at the interfaces between ridges 360 and the nicotine or lactic acid sources 210/220. More specifically, the mesh susceptors 340 are configured to partition each of the first compartment 310 and second compartment 320 such that the sources 210,220 and flow channels 350 formed between the ridges 360 are separated from each other.

In this example, the heater cavities 140 in cartridge 100 of FIG. 4 are not present. Due to the absence of such heater cavities, the end cap heater cavities 136 as featured in cartridge 100 of FIG. 4 are also not present in end caps 330. The absence of such cavities allows larger first and second compartments 110,120 in the cartridge 300. As a result, thicker nicotine and lactic acid sources 210,220, e.g. ones with larger storage capacities, may be used.

In use, the inductor coil 28 induces eddy currents in the mesh susceptors, causing the mesh susceptors 340 to heat up. Because of its mesh construction, the mesh susceptors 340 permit vaporized nicotine and lactic acid at the surface of their respective sources 210,220 to escape into their respective air flow channels 350. Since heating takes place at the surface of the nicotine and lactic acid sources 210,220, vaporized nicotine and lactic acid no longer have to percolate through the depth of the sources to be extracted at their respective surfaces. Therefore, such arrangement allows a more efficient extraction of vaporized nicotine and lactic acid.

The mesh susceptors 340 are supported by the ridges in the first and second compartments 310, 320. This allows the mesh susceptors 340 to be formed from materials with lower mechanical strength. In other words, the mesh susceptors may be formed from flexible materials and do not need to sustain their own weight.

Figure 10:
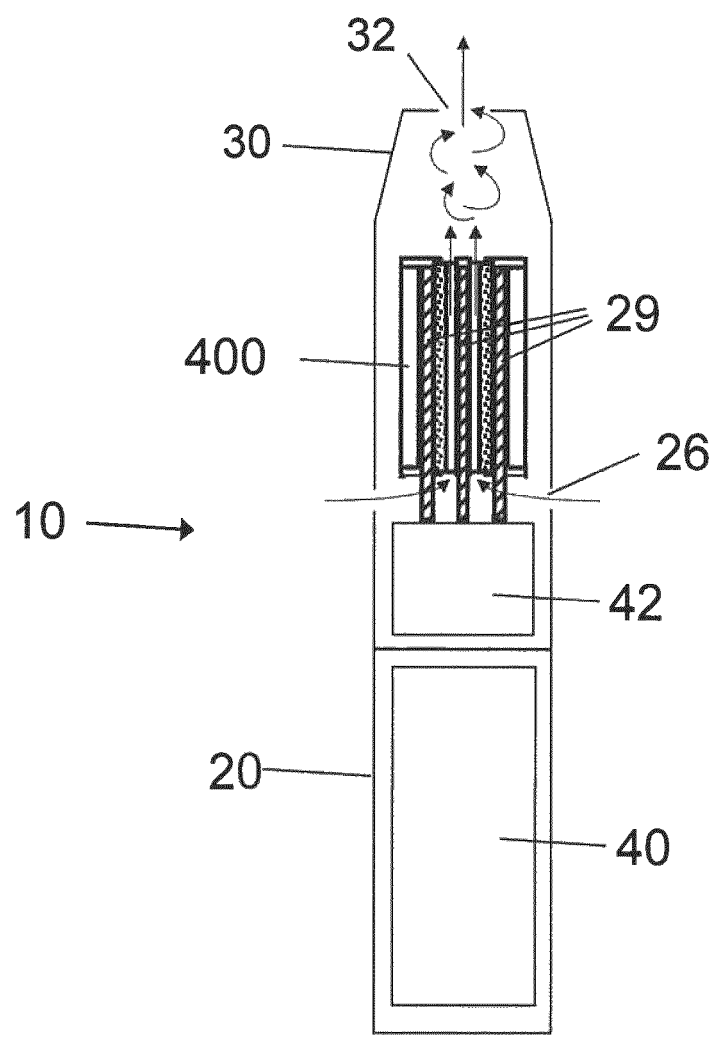
FIG. 10 is a sectional view of an aerosol-generating system according to yet another embodiment of the present invention.

In yet another embodiment as shown in FIG. 10, the inductor coil 28 in the aerosol-generating device 20 and the susceptors are replaced by a plurality of resistive heating elements 29. In this embodiment the resistive heating elements are part of the aerosol-generating device 20. During use, the controller 42 controls the power supply to the resistive heating elements 29 to heat the nicotine source 210 and lactic acid source 220.

The plurality of resistive heating elements 29 are elongate electric heaters positioned in the cavity 22 of the aerosol-generating device 20. The elongate electric heaters extend along the longitudinal axis of the cavity 22 and are each arranged to fit into a corresponding heater cavity of the cartridge 400.

In comparison to the end cap 130 of FIG. 5, a modified distal end cap is provided for the cartridge 400 in this embodiment. The end cap heater cavities 136 in FIG. 6 are replaced by open heater slots extending through the depth of the distal end cap. Through these heater slots, the heater elements 29 of the aerosol-generating device 20 extend into the heater cavities of the cartridge body. In this particular embodiment, the heater slots are configured to provide a snug fit to the resistive heating elements 29. Thus allowing the cartridge 400 to be supported by the heating elements 29 when it is inserted into the cavity 22 of the aerosol-generating device 20.

Prior to first use of the cartridge 100, the air inlets 132,134 and the air outlets 133,135 are sealed by a removable peel-off foil seal (not shown) applied to the outwardly facing surface of the end caps 130. This reduces loss of nicotine and lactic acid to the atmosphere, thus lengthening the shelf life of the cartridge. In addition, the foil seal prevents contamination of the nicotine source 210 and the lactic acid source 220.

The exemplary embodiments described above illustrate but are not limiting. In view of the above discussed exemplary embodiments, other embodiments consistent with the above exemplary embodiments will now be apparent to one of ordinary skill in the art.

The invention claimed is:

1. A cartridge for use in an aerosol-generating system, the cartridge comprising:
a first compartment having a first air inlet and a first air outlet, the first compartment containing a nicotine source; and a second compartment having a second air inlet and a second air outlet, the second compartment containing an acid source;
wherein the first compartment comprises a first air flow channel extending from the first air inlet, or the first air outlet, longitudinally along at least a portion of the first compartment, wherein the first air flow channel is adjacent to and in fluid communication with the nicotine source; or
wherein the second compartment comprises a second air flow channel extending from the second air inlet, or the second air outlet, longitudinally along at least a portion of the second compartment, wherein the second air flow channel is adjacent to and in fluid communication with the acid source; or
wherein the first compartment comprises a first air flow channel extending from the first air inlet, or the first air outlet, longitudinally along at least a portion of the first compartment, wherein the first air flow channel is adjacent to and in fluid communication with the nicotine source; and the second compartment comprises a second air flow channel extending from the second air inlet, or the second air outlet, longitudinally along at least a portion of the second compartment, wherein the second air flow channel is adjacent to and in fluid communication with the acid source,
wherein at least one of the first air flow channel and the second air flow channel is at least partially defined by one or more protrusions extending from an interior wall of the respective first compartment or second compartment, and wherein the one or more protrusions are configured to provide support for the nicotine source or the acid source.

2. The cartridge according to claim 1, wherein the first air flow channel extends between the first air inlet and the first air outlet; or wherein the second air flow channel extends between the second air inlet and the second air outlet, or wherein the first air flow channel extends between the first air inlet and the first air outlet and the second air flow channel extends between the second air inlet and the second air outlet.

3. The cartridge according to claim 2, wherein at least one of the first air flow channel and the second air flow channel extends along the length of the respective nicotine source or acid source.

4. The cartridge according to claim 1, wherein the one or more protrusions are ridges extending along the interior wall of the compartment, and wherein at least one of the first air flow channel and the second air flow channel is formed between said ridges.

5. The cartridge according to claim 1, wherein the nicotine source comprises a porous ceramic impregnated with nicotine, or the acid source comprises a porous ceramic impregnated with acid, or the nicotine source comprises a first porous ceramic impregnated with nicotine and the acid source comprises a second porous ceramic impregnated with acid.

6. The cartridge according to claim 1, wherein the first air flow channel and the second air flow channel are arranged in parallel within the cartridge.

7. The cartridge according to claim 1, wherein at least one of the nicotine source and the acid source is partitioned from the respective first air flow channel and the second air flow channel by one or more mesh heating elements, wherein each of the one or more mesh heating elements comprises one or more openings through which fluid can pass.

8. The cartridge according to claim 7, wherein the one or more mesh heating elements comprise one or more susceptors configured to heat at least one of the nicotine source and the acid source when exposed to a changing magnetic flux produced by an inductor coil.

9. The cartridge according to claim 1 further comprising a cavity located between the first compartment and the second compartment for receiving a heater configured to heat the first compartment and the second compartment.

10. The cartridge according to claim 1, wherein the ratio of flow area of the first air inlet to the flow area of the second air inlet is between about 3:4 and about 1:2.

11. The cartridge according to claim 1, wherein the flow area of the first air inlet is between about 0.1 square millimetres and about 1.6 square millimetres and the flow area of the second air inlet is between about 0.2 square millimetres and about 2.4 square millimetres.

12. An aerosol-generating system comprising:
the cartridge according to claim 1; and
an aerosol-generating device comprising:
a housing defining a cavity for receiving at least a portion of the cartridge; and
a heater for heating the first compartment and the second compartment of the cartridge.

\* \* \* \* \*